United States Patent [19]

Edington et al.

[11] 4,180,670

[45] Dec. 25, 1979

[54] AMINO PYRIDINE DERIVATIVES

[75] Inventors: Edwin T. Edington, Maidenhead; Alan C. White, Windsor, both of England

[73] Assignee: John Wyeth & Brother Limited, Maidenhead, England

[21] Appl. No.: 873,192

[22] Filed: Jan. 30, 1978

[30] Foreign Application Priority Data

Feb. 2, 1977 [GB] United Kingdom ............... 4354/77
Jul. 9, 1977 [GB] United Kingdom ............ 28879/77

[51] Int. Cl.² .......................................... C07D 213/38
[52] U.S. Cl. .................................. 546/284; 546/270; 546/304; 546/312
[58] Field of Search ....... 260/296 D, 296 R, 294.8 D; 546/270, 284, 304, 312, 255

[56] References Cited

U.S. PATENT DOCUMENTS 2,974,139  3/1961  Schuler al. ............................ 546/304
3,926,611  12/1975  Tomlin et al. ........................ 546/304

OTHER PUBLICATIONS

Carpenedo et al., Chem. Abstracts, vol. 73, p. 236, item 108,061s, (1970).

*Primary Examiner*—Alan L. Rotman
*Attorney, Agent, or Firm*—Arthur E. Wilfond

[57] ABSTRACT

Novel 4-pyridinamine derivatives having the formula

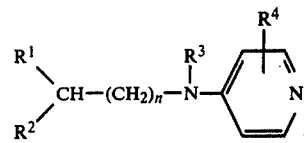

[where $R^1$ and $R^2$ are aryl or heteroaryl (optionally linked together by a lower alkylene bridge) or one of $R^1$ and $R^2$ is aryl or heteroaryl and the other of $R^1$ and $R^2$ is lower alkyl or ar(lower)alkyl, $R^3$ and $R^4$ are each hydrogen or lower alkyl and n is 0 or 1] and their non-toxic acid addition salts are described. They show CNS activity and may be used as antidepressant drugs. Some also show stimulant activity.

Novel intermediates having the formula

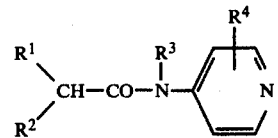

are also described.

9 Claims, No Drawings

AMINO PYRIDINE DERIVATIVES

The invention relates to novel pyridine derivatives which show pharmaceutical activity, particularly CNS activity. The invention provides the new pyridine derivatives, processes for their preparation and pharmaceutical compositions containing the new pyridine derivatives.

The invention provides novel pyridine derivatives having the formula I

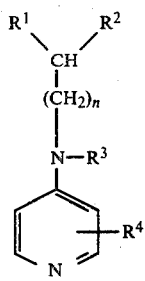

and their pharmaceutically acceptable acid addition salts, wherein $R^1$ and $R^2$ together represent —$Ar^1$—(-lower alkylene)—$Ar^2$—where $Ar^1$ and $Ar^2$ are independently arylene or heteroarylene, or when $R^1$ and $R^2$ are separate one of $R^1$ and $R^2$ represents aryl or heteroaryl and the other one of $R^1$ and $R^2$ represents aryl, heteroaryl, ar(lower)alkyl or lower alkyl, $R^3$ and $R^4$ are independently hydrogen or lower alkyl and n represents 0 or 1. The invention particularly includes those cases where $R^1$ and $R^2$ are independently aryl or heteroaryl whilst n is 0.

By the term "lower" as used herein in connection with such groups as alkyl, alkylene and alkoxy, there is meant that the group contains up to 6 carbon atoms, preferably up to 4 carbon atoms. By the term "aryl or heteroaryl" there is meant a monovalent group having aromatic character. By the term "arylene or heteroarylene" there is meant a divalent group having aromatic character. The groups having aromatic character may be carbocyclic or heterocyclic and the aromatic ring or rings may be unsubstituted or carry one or more substituents.

$R^1$ and $R^2$ may be the same or different aromatic groups. Examples of aryl groups include phenyl; naphthyl phenyl substituted by one or two substituents, for example, halogen, for instance, fluorine, chlorine or bromine; lower alkyl, for instance, methyl, ethyl, propyl or butyl; lower alkoxy, for instance methoxy, ethoxy, propoxy or butoxy; lower alkylenedioxy, for instance methylenedioxy and trihaloalkyl, for instance, trifluoromethyl. The aryl group preferably has a monocyclic aromatic ring but may be bicyclic, for instance, naphthyl or naphthyl carrying one or more substituents, for example, those mentioned above in connection with substitution of phenyl. Examples of heteroaryl groups include furyl (for example, 3-furyl), thienyl (for example, 2-thienyl), oxazolyl, thiazolyl, benzthiazolyl, pyridyl (for example 2- and 4-pyridyl), quinolyl (for example 2-quinolyl) and isothiazolyl (for example, 5-isothiazolyl). The heteroaryl groups may be unsubstituted or substituted as described above for the substitution of phenyl. Preferred heteroaryl groups are thienyl, pyridyl and furyl.

One of $R^1$ and $R^2$ may be an aryl or heteroaryl group as described above whilst the other of $R^1$ and $R^2$ may be lower alkyl, for example, methyl, ethyl, propyl, butyl or pentyl, or ar(lower)alkyl, for instance, phen(lower)alkyl, e.g. benzyl or phenethyl. When $R^1$ and $R^2$ are connected together the two arylene or heteroarylene groups may be the same or different. The groups may be divalent groups corresponding to the aryl and heteroaryl groups particularly described above, for instance, phenylene. The lower alkylene group may be, for example, methylene, ethylene or trimethylene. The preferred meanings of $R^1$ and $R^2$ are as follows. One of $R^1$ and $R^2$ is phenyl, (lower alkyl)phenyl, (lower alkoxy)phenyl, halophenyl, thienyl or pyridyl whilst the other of $R^1$ and $R^2$ ie phenyl, (lower alkyl)phenyl, (lower alkoxy)phenyl, halophenyl, thienyl, pyridyl, phen(lower)alkyl or lower alkyl or $R^1$ and $R^2$ together represent—phenylene—(lower alkylene)—phenylene—.

$R^3$ and $R^4$ may be the same or different and are selected from hydrogen and lower alkyl, for example, methyl, ethyl, propyl and butyl. $R^3$ and $R^4$ are preferably chosen from hydrogen and methyl.

The acid addition salts may be formed from inorganic acids and organic acids and examples include the sulphate, hydrochloride, hydrobromide, hydroiodide, nitrate, phosphate, sulphonate (such as the methane sulphonate and toluene-p-sulphonate), acetate, maleate, fumarate, tartrate and formate.

It will be apparent to the reader that the compounds having formula I where $R^1$ and $R^2$ differ possess an asymmetric carbon atom and thus exhibit the property of optical isomerism. The invention includes the individual optical isomers as well as the racemic mixtures. The racemates may be resolved into individual optical isomers in known manner.

The compounds of general formula I and their acid addition salts can be prepared in a number of ways by building up the molecule from suitable starting materials in known manner. A choice of methods exists so that the most appropriate one may be chosen in each case. In particular the compounds may be prepared by reduction of amides, conversion of primary amines into secondary amines or conversion of secondary amines into tertiary amines, by rotation of an organometallic compound with Schiff's bases, by reaction of benzilic acid with aminopyridines and by reduction of Schiff's bases.

The invention provides a process for the preparation of a compound having formula I or a pharmaceutically acceptable acid addition salt thereof, wherein (a) a compound having the formula III

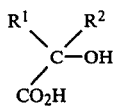

(wherein $R^1$ and $R^2$ are as defined above, preferably phenyl or the like) is reacted under elevated temperature with a 4-aminopyridine having the formula IV

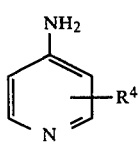

(where $R^4$ is as defined above) to form a compound having the formula

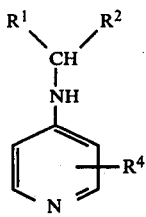

(where $R^1$, $R^2$ and $R^4$ are as defined above); or (b) a compound having the formula

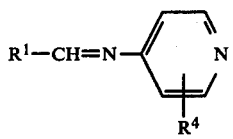

(VI)

(where $R^1$ and $R^4$ are as defined above) is treated with a reactive organometallic compound whose organo moiety is $R^2$ as defined above; or (c) an amine having the formula VII

(VII)

or a salt thereof, is teacted with a compound having formula VIII

Y—Z (VIII)

(where Z is a replaceable atom or group) to form an amine having the formula IX

(IX)

as a free base or acid addition salt (where in formulae VII, VIII and IX any one of W, X and Y represents a group having the formula

(X)

(where $R^1$, $R^2$ and n are as defined above), another one of W, X and Y represents a group having the formula

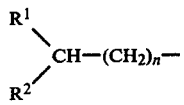

(XI)

(where $R^4$ is as defined above) and the remaining one of W, X and Y represents $R^3$ as defined above subject to the proviso that, when Y represents $R^3$ as defined above, then $R^3$ is lower alkyl); or (d) a Schiff's base having the formula XII or XIII

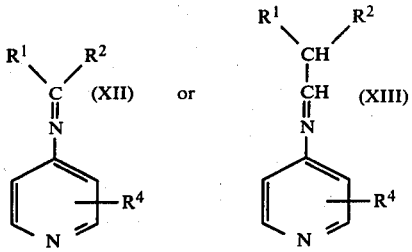

(wherein $R^1$, $R^2$ and $R^4$ are as defined above) is reduced; or (e) an amide having the formula XIV

(XIV)

or an acid addition salt thereof (wherein $R^1$, $R^2$, $R^3$ and $R^4$ are as defined above) is reduced to form a compound where n is 1. Where desired, the process may include conversion of a free base form of the compound having formula I into a pharmaceutically acceptable acid addition salt thereof or conversion of an acid addition salt form of a compound having formula I into its free base form.

Where it is desired to form an end product in which $R^1$ or $R^2$ contains a reactive group, the group may be protected in the starting material, i.e. $R^1$ represents a protected form of $R^1$ or $R^2$ represents a protected form of $R^2$. For example, where $R^1$ or $R^2$ represents aminophenyl, the starting material may contain a protecting group for the amino function. Many protecting groups will suggest themselves to those skilled in the art. When a protecting group is employed we prefer to use one which can be removed under mild conditions.

The starting materials for methods (a), (b) and (c), namely those having formulae III, IV, VI, VII and VIII and the reactive organometallic compound are sometimes known and, where new, can be prepared in known manner. The compounds having general formula XIV and their acid addition salts are new compounds also provided by the invention. They can be prepared in manner known per se. In particular an amine having the formula

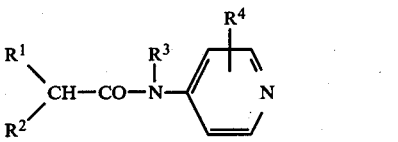

(XV)

(where $R^3$ and $R^4$ are as defined above) is acylated to introduce the acyl group

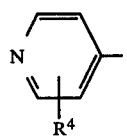

(XVI)

(where $R^1$ and $R^2$ are as defined above).

The acylation may be performed using the acyl halide, for instance, the acyl chloride or acyl bromide, in the presence of a suitable base. The Schiff's bases of formulae XII and XIII are sometimes known [see, for example, Chemical Abstracts (1972), 77, 88002a] or, if new, obtainable in known manner.

We prefer to carry out method (a) by using benzilic acid as the compound having formula III. The reaction is preferably carried out by heating the reactants at an appropriate temperature, which may be about 180° C. to 230° C., in the absence of a solvent.

The compounds having the formula VI are Schiff's bases which can be prepared in known manner by condensation of an aldehyde of formula $R^1CHO$ with an amine having formula IV. Method (b) is preferably carried out by using a compound having the formula $R^2Li$ as the organometallic compound. Alternatively a Grignard reagent such as phenyl magnesium bromide may be employed.

The reaction is preferably carried out in an inert solvent such as ether under an inert atmosphere such as nitrogen. The reaction yields an amine having formula V in the form of a salt such as the lithium salt. Decomposition of the resulting reaction complex with ice water or a cold solution of ammonium chloride gives the amine which can be recovered in standard manner.

Method (c) can be carried out using known procedures for converting primary amines into secondary amines and secondary amines into tertiary amines. We prefer to use a compound of formula VIII in which Z is halogen, particularly bromine or chlorine.

The starting amine may be used as such or in the form of a salt thereof, for instance, the lithium salt. An example of the use of the salt is as follows: An organometallic compound such as the lithium salt having the formula $R^2Li$ is reacted with a Schiff's base having formula VI to give a compound having the formula V in the form of its lithium salt having the formula XVII

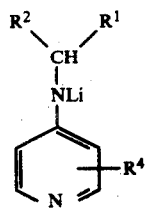

(XVII)

This procedure may be carried out as described under method (b). However instead of treating the salt with water as in method (b) the lithium salt is treated with a lower alkyl halide, for example, methyl chloride or ethyl bromide, to effect alkylation to result in a tertiary amine in which $R^3$ is lower alkyl.

Method (c) may also be used to form secondary amines. For example a compound having the formula

W—NH$_2$ may be treated with a compound having formula Y—Z (where one of W and Y represents a group having formula X and the other represents a group having formula XI) to form a secondary amine of formula W—NH—Y. We prefer to carry out this method by reacting an appropriately substituted methyl halide of formula XVIII

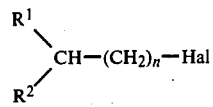

(XVIII)

(where Hal is halogen such as chlorine or bromine and n is 0 or 1) with an amine having the formula IV.

The reaction of the amine having formula VII with the compound having formula VIII may be carried out under elevated temperature in a suitable solvent, for example, toluene.

The reduction according to method (d) may be carried out under conditions known for the reduction of Schiff's bases to form amines. As reducing agent there may be used lithium aluminum hydride or sodium borohydride. In particular, the reduction may be performed using sodium borohydride in an alcohol, for instance, methanol or ethanol, at room temperature. The reduction may also be carried out using lithium aluminium hydride in ether at room temperature or under reflux. Catalytic hydrogenation may be used. The reduction conditions employed should be so chosen as to avoid reduction of the pyridine ring and/or cleavage of the di(aryl or heteroaryl)methyl group —$CHR^1R^2$.

It will be appreciated that where $R^1$ or $R^2$ in the starting products contains a reducible group, this may be reduced under the reaction conditions, for example, a nitrophenyl group may be reduced to aminophenyl.

It will be appreciated that the reduction products obtained from Schiff's bases of formula XII are compounds where n is 0 and $R^3$ is hydrogen and those obtained from Schiff's bases of formula XIII are compounds where n is 1 and $R^3$ is hydrogen.

The reduction according to method (e) may be carried out under conditions known for the reduction of amides to form amines. As reducing agent there may be used lithium aluminium hydride or diborane. It will be appreciated that the reduction products obtained are compounds where n is 1.

When a product of formula I has been prepared in the form of its free base this may be converted into an acid addition salt by addition of an acid. For example, ethereal hydrogen bromide or ethereal hydrogen chloride may be added to a solution of the free base to give the hydrobromide or hydrochloride salt respectively. Acid addition salt forms of compounds having formula II may be converted into the free base form in known manner, in particular, by addition of a base.

The compounds having formula I and their pharmaceutically acceptable acid addition salts are indicated for pharmaceutical use. In particular they show CNS (central nervous system) activity, when tested on warm blooded animals. They reverse the hypothermia induced by reserpine on mice and thus may have potential use as antidepressant drugs. Some show stimulant activity. For example, the compound of Examples 1 and 2 exhibited stimulant activity in mice when tested at doses of 1.27 and 4 milligrams per kilogram administered orally and intraperitoneally.

The invention also includes pharmaceutical compositions containing as active ingredient a compound of formula I or a pharmaceutically acceptable acid addition salt thereof which may be micronised if desired. In addition to the active ingredient said compositions also contain a pharmaceutically acceptable carrier. Any suitable carrier known in the art can be used to prepare the pharmaceutical compositions. In such a composition, the carrier may be a solid, liquid or mixture of a solid and a liquid. Solid form compositions include powders, tablets and capsules. A solid carrier can be one or more substances which may also act as flavouring agents, lubricants, solubilisers, suspending agents, binders or tablet-disintegrating agents; it can also be an encapsulating material. In powders the carrier is a finely divided solid which is in admixture with the finely divided active ingredient. In tablets the active ingredient is mixed with a carrier having the necessary binding properties in suitable proportions and compacted in the shape and size desired. The powders and tablets preferably contain from 5 to 99, preferably 10-80%, by weight of the active ingredient. Suitable solid carriers are magnesium carbonate, magnesium stearate, talc, sugar, lactose, pectin, dextrin, starch, gelatin, tragacanth, methyl cellulose, sodium carboxymethyl cellulose, a low melting wax, and cocoa butter. The term "composition" is intended to include the formulation of an active ingredient with an encapsulating material as carrier to give a capsule in which the active ingredient (with or without other carriers) is surrounded by carrier, which is thus in association with it. Similarly cachets are included.

Sterile liquid form compositions include sterile solutions, suspensions, emulsions, syrups and elixirs. The active ingredient can be dissolved or suspended in a pharmaceutically acceptable sterile liquid carrier, such as sterile water, a sterile organic solvent or a mixture of both. Preferably a liquid carrier is one suitable for parenteral injection. Where the active ingredient is sufficiently soluble it can be dissolved in a suitable organic solvent, for instance aqueous propylene glycol or polyethylene glycol solutions. Aqueous propylene glycol containing from 10 to 75% of the glycol by weight is generally suitable. In other instances compositions can be made by dispersing the finely-divided active ingredient in aqueous starch or sodium carboxymethyl cellulose solution, or in a suitable oil, for instance arachis oil. Liquid pharmaceutical compositions which are sterile solutions or suspensions can be utilised by intramuscular, intraperitoneal or subcutaneous injection. In many instances a compound is orally active and can be administered orally either in liquid or solid composition form.

Preferably the pharmaceutical composition is in unit dosage form. In such form, the composition is subdivided in unit doses containing appropriate quantities of the active ingredient; the unit dosage form can be a packaged composition, the package containing specific quantities of compositions, for example, packeted powders or vials or ampoules. The unit dosage form can be a capsule, cachet or tablet itself, or it can be the appropriate number of any of these in package form. The quantity of active ingredients in a unit dose of composition may be varied or adjusted from 5 mg or less to 500 or more, according to the particular need and the activity of the active ingredient. The invention also includes the compounds in the absence of carrier where the compounds are in unit dosage form.

The following Examples illustrate the invention:

EXAMPLE 1

N-(Diphenymethyl)-4-pyridinamine

A mixture of 11.4 grams (0.05 mole) of benzilic acid and 4.7 grams (0.05 mole) of 4-aminopyridine was heated at 220° C. for 3.5 hours. After cooling the mixture was dissolved in toluene and washed with 10% sodium carbonate solution and with 2 N hydrochloric acid. The acidic extracts were basified with 5 N sodium hydroxide and the resulting oil extracted into toluene. After drying over magnesium sulphate, the toluene was removed and the yellow oil was recrystallised from light petroleum (b.p. 80°-100° C.) giving 1.35 grams (10% yield) of the title compound, m.p. 152° to 154° C.

EXAMPLE 2

N-(Diphenylmethyl)-4-pyridinamine 24.7 Grams (0.1 mole) of diphenylbromomethane and 29.4 grams (0.3 mole) of 4-aminopyridine in 500 milliliters of toluene were heated under reflux with stirring for 20 hours. The solid formed was filtered off and the toluene was extracted with 2 N hydrochloric acid. The acid extracts were combined with the solid material and the solid was taken into solution by the addition of water and methanol. The alcoholic solution was basified with 5 N sodium hydroxide and extracted with toluene. After drying over magnesium sulphate, the solvent was removed and 8.01 grams of the title compound were obtained as the crude crystalline base, m.p. 148°-50° C. The base was converted into its hydrochloride by solution in the minimum quantity of 2-propanol and addition of a solution of hydrogen chloride in dry ether. The hydrochloride was obtained as a colourless solid, m.p. 237°-9° C.

Analysis: Found: C, 72.1%; H, 5.9%; N, 8.8%. $C_{18}H_{16}N_2.HCl.\frac{1}{4}H_2O$ requires C, 71.75%; H, 5.84%; N, 9.3%.

EXAMPLE 3

N-[di-p-fluorophenyl)methyl]-4-pyridinamine 8.85 Grams (0.03 mole) of chlorodi(p-fluorophenyl)methane and 11.75 grams (0.125 mole) of 4-aminopyridine in 250 milliliters of toluene were heated under reflux with stirring. After 8 hours, the reaction mixture was cooled and filtered to recover unreacted 4-aminopyridine. The toluene solution was extracted with 2 N hydrochloric acid and the acid extracts were basified with 5 N sodium hydroxide and extracted into toluene. After washing with water, the basic extracts were dried over magnesium sulphate and evaporated to give a 3.51 grams of a crystalline solid. The solid was recrystallised from toluene or a mixture of toluene and light petroleum (b.p. 60°-80° C.) to afford 3.13 grams (28% yield) of colourless crystals of the title compound, m.p. 150°-153° C.

Analysis: Found: C, 73.2%; H, 4.9%; N, 9.4%. $C_{18}H_{14}F_2N_2$ requires C, 72.95%; H, 4.8%; N, 9.2%.

EXAMPLE 4

N-[α-(2-methylphenyl)benzyl]-4-pyridinamine

250 Milliliters of toluene containing 10.8 grams (0.05 mole) of chloro(phenyl-o-tolyl)methane and 14.1 grams (0.15 mole) of 4-aminopyridine were heated under reflux with stirring for 20 hours. The reaction mixture was cooled and the resulting organic layer and solid material were stirred with 2 N hydrochloric acid. The toluene layer was removed and the gummy acidic extracts were basified with 5 N sodium hydroxide. The resulting oil was extracted into toluene and washed with water. After drying over magnesium sulphate, the solvent was removed and the residue was recrystallised from toluene to afford 3.58 grams (31% yield) of the title compound, m.p. 141°-143° C. The product may be recrystallised from a mixture of benzene and light petroleum (b.p. 100°-120° C.).

Analysis: Found: C, 83.3%; H, 6.8%; N, 9.9%. $C_{19}H_{18}N_2$ requires C, 83.2%; H, 6.6%; N, 10.2%.

EXAMPLE 5

N-[α-(2-thienyl)benzyl]-4-pyridinamine 0.03 Mole of butyl lithium in hexane as a 15% w/w solution, was added dropwise to a stirred solution of 2.52 grams (0.03 mole) of thiophene in 50 milliliters of anhydrous ether under dry nitrogen. 4.55 Grams (0.025 mole) of benzylideneaminopyridine in 50 milliliters of dry ether was then added dropwise to the reaction mixture keeping the temperature below 10° C. The yellow precipitate obtained was stirred at room temperature for 6 hours and poured onto ice. The organic layer was separated and extracted with 2 N hydrochloric acid and the acid extracts were combined with the aqueous layer. The resultant aqueous medium was basified with 5 N sodium hydroxide solution and then extracted with dichloromethane. After drying over magnesium sulphate, the solvent was removed to leave a solid which was recrystallised from a mixture of toluene and light petroleum (b.p. 100°-120° C.) to afford 2.67 grams of title compound, m.p. 125°-126° C.

Analysis: Found: C, 72.0%; H, 5.5%; N, 10.5%. $C_{16}H_{14}N_2S$ requires C, 72.15%; H, 5.3%; N, 10.5%.

The hydrochloride salt of the title compound, m.p. 224° C. (decomposition), was prepared by dissolving the base in 2-propanol and treating with a solution of hydrogen chloride in dry ether.

Analysis: Found: C, 63.6%; H, 5.15%; N, 9.1%. $C_{16}H_{14}N_2S.HCl$ requires C, 63.5%; H, 5.0%; N, 9.25%.

EXAMPLE 6

N-[α-(2-methoxyphenyl)benzyl]-4-pyridinamine 2.98 Grams (0.016 mole) of 4-benzylideneaminopyridine in 50 milliliters of dry ether were added dropwise to a stirred solution of 2-methoxyphenyl lithium (prepared from 0.03 mole of butyl lithium and 5.61 grams [0.03 mole] of o-bromoanisole) in a mixture of ether and hexane at 0° C. under nitrogen. The mixture was stirred at room temperature for 2 hours and then poured onto ice. The organic layer was separated and extracted with acid and the acid extracts were combined with the aqueous layer. The combined aqueous medium was basified with 5 N sodium hydroxide and extracted into dichloromethane. After drying over magnesium sulphate, the solvent was removed to leave a solid which yielded 2.3 grams of title compound, m.p. 143°-5° C. The product was converted into its hydrobromide salt, m.p. 196°-198° C., by solution in 2-propanol and addition of hydrogen bromide in dry ether.

Analysis: Found: C, 61.6%; H, 5.3%; N 7.6%. $C_{19}H_{18}N_2O.HBr$ requires C, 61.45%; H, 5.2%; N, 7.5%.

EXAMPLE 7

N-(α-[2-pyridyl]benzyl)-4-pyridinamine 4.55 Grams (0.025 mole) of 4-benzylideneaminopyridine in 50 milliliters of dry ether was added dropwise to a stirred solution of 2-pyridyl lithium (prepared from 0.03 mole of butyl lithium and 4.74 grams [0.03 mole] of 2-bromopyridine) in 100 ml. of hexane-ether cooled to −30° C. under nitrogen. A purple precipitate was formed which was stirred for 4 hours while allowing the product to warm up to room temperature. The mixture was poured onto ice and the organic layer was separated and extracted with 2 N hydrochloric acid. The acid extracts were combined with the aqueous layer and the combined aqueous medium was basified with 5 N sodium hydroxide and extracted into dichloromethane. After drying over magnesium sulphate, the solvent was removed to leave a solid which was recrystallized from a mixture of toluene and light petroleum (b.p. 100°-120° C.) to afford 2.27 grams of the title compound as free base, m.p. 114°-115° C. The base was converted to its colourless dihydrobromide salt, m.p. 230° (decomposition), by dissolution in the minimum quantity of 2-propanol and adding a solution of hydrogen bromide in dry ether.

Analysis: Found: C, 48.3%; H, 4.23%; N, 10.1%. $C_{17}H_{15}N_3.2HBr$ requires C, 48.25%; H, 4.05%; N, 9.9%.

EXAMPLE 8

N-(10,11-dihydro-5H-dibenzo[a,d]cyclohepten-5-yl)-4-pyridinamine 10.3 Grams (45 millimoles) of 5-chloro-10,11-dihydro-5H-dibenzo[a,d]cycloheptene and 7.05 grams (75 millimoles) of 4-aminopyridine were heated together in 150 cc of dry toluene under reflux for 24 hours. After cooling, the toluene solution was decanted, washed twice with 75 cc of water and then washed twice with 2 N hydrochloric acid (50 cc each time). A solid then precipitated at the interface. This solid (A) was collected and amounted to 1.42 grams. A gum also precipitated on the vessel walls, and was separated from the toluene and aqueous phases, hich contained only unreacted starting materials. This gum was washed with 2 N hydrochloric acid and was then dissolved in chloroform, dried (MgSO4), and evaporated, leaving 1.34 grams of a foam. Extraction of this foam with a little chloroform left 1.0 gram of an insoluble solid (B).

Solid (B) was crystallised from ethyl acetate/methanol, giving 0.58 grams of (N-10,11-dihydro-5H-dibenzo[a,d]cyclohepten-5-yl-4-pyridinamine)hydrochloride as colourless crystals, melting point 267°-8°.

Analysis: Found C, 74.7%; H, 6.2%; N, 8.4%. $C_{20}H_{18}N_2.HCl$ requires C, 74.4%; H, 5.9%; N, 8.7%, Further less pure material (0.77 grams) of melting point 263°-4° was obtained by crystallisation of solid (A) from ethyl acetate-methanol.

EXAMPLE 9

N-[α-butyl-2-thenyl]-4-pyridinamine

To a stirred, cooled (10°-20° C.) a solution of 3.77 grams of 4-(2-thenylideneamino)pyridine in 100 milliliters of dry ether, a solution containing 0.025 mole butyl lithium in 50 milliliters of dry ether was added dropwise. The resulting solution was stirred at room temperature for 4 hours, and then diluted with 150 ml dry ether before cautious addition of 50 ml. water. The organic phase was dried (MgSO4) and evaporated to dryness to give 5.24 grams of a brown oil. This brown oil was dissolved in toluene and extracted with 2 N hydrochloric acid. The extracts were basified with sodium hydroxide and extracted back into toluene. The resulting solution of the base in toluene was dried (MgSO4) and evaporated to dryness. The resulting oil was crystallised from petrol (100°-120° C.)/toluene affording 2.0 grams of a white solid. This material was dissolved in isopropanol and converted to the hydrochloride salt with ethereal hydrogen chloride and crystallised by addition of ether, yielding 1.153 grams of N-[α-butyl-2-thenyl]-4-pyridinamine hydrochloride of melting point 146.5°-148° C.

Analysis: Found C, 59.27%; H, 6.95%; N, 9.93%. $C_{14}H_{18}N_2.HCl$ requires C, 59.45%; H, 6.77%; N, 9.90%.

EXAMPLE 10

N-(2,2-diphenylethyl)4-pyridinamine

Diborane (generated from 0.033 moles $NaBH_4$ and 0.06 moles $BF_3/Et_2O$) was swept by a stream of nitrogen into a flask containing 2.16 grams (7.5 millimoles) of N-(4-pyridyl)diphenyl acetamide in 50 milliliters of dry tetrahydrofuran stirred and cooled to 0° C. When all diborane had been formed, the reaction mixture was heated under reflux for 3 hours and then left overnight at room temperature. The mixture was cooled to 0° C. and 10 milliliters of 6 N hydrochloric acid was added. The tetrahydrofuran was removed at atmosphere pressure. The product was neutralized with 5 N sodium hydroxide, extracted into ether, dried ($MgSO_4$) and evaporated to an oil which solidified. After trituration with ether, 1.46 g (71% yield) of fine felted needles were obtained. The title compound was converted to its hydrochloride by solution in isopropyl alcohol/HCl/$Et_2O$. 1.18 Grams of product m.p. 205°-207°, were obtained.

Analysis: Found C, 73.48%; H, 6.28%; N, 9.07%. $C_{19}H_{18}N_2HCl$ requires C, 73.56%; H, 6.16%; N, 9.03%.

The N-(4-pyridyl)diphenylacetamide starting material was prepared as follows:

9.4 Grams (0.1 mole) of 4-aminopyridine and 11.5 grams (0.05 mole) of diphenyl acetyl chloride were stirred together at room temperature in 65 milliliters of pyridine for 4.5 hours. Te resulting mixture was poured into water and extracted with toluene. The organic phase was separated, dried ($MgSO_4$) and the toluene removed. The resulting solid was recrystallised from toluene yielding 10.9 g α-phenyl-N-(4-pyridinyl)benzene acetamide m.p. 166.5°-168° C. The fumarate salt was prepared by dissolving equimolar quantities of the free base and fumaric acid in hot 2-propanol and allowing the product to crystallise. Melting point 171°-173° C.

Analysis: Found: C, 68.2%; H, 5.25%; N, 6.7%. $C_{19}H_{16}N_2O.C_4H_4O_4$ requires: C, 68.3%; H, 5.0%; N, 6.7%.

EXAMPLE 11

N-([α-phenyl]-n-pentyl)-4-pyridinamine 0.03 Mole of butyl lithium in hexane as a 15% w/w solution was added dropwise to a stirred, cooled (−10° C.) solution of 5.46 grams (0.03 mole) of 4-benzylideneamino pyridine in 10 milliliters of dry ether. The mixture was allowed to warm to room temperature and then poured onto ice and extracted with methylene chloride. The organic phase was separated and extracted with 2 N hydrochloric acid. The extracts were basified with 2 N sodium hydroxide and extracted into methylene chloride. The resulting methylene chloride solution was dried ($MgSO_4$) and decolourised with charcoal. The solvent was removed and the resulting light oil (5.75 grams) was crystallised and recrystallised from a toluene/petrol (60°-80° C.) mixture affording 2.36 grams of N-([α-phenyl]-n-pentyl)-4-pyridinamine, melting point 118°-8.5°.

Analysis: Found: C, 79.94%; H, 8.40%; N, 11.58%. $C_{16}H_{20}N_2$ requires C, 79.97%; H, 8.39%; N, 11.66%.

The hydrochloride salt was prepared by dissolving the base in 2-propanol and treating with a solution of hydrogen chloride in dry ether. The salt had a melting point of 155.5°-157° C.

Analysis: Found: C, 69.13%; H, 7.60%; N, 10.03%. $C_{16}H_{21}N_2Cl$ required C, 69.43%; H, 7.65%; N, 10.12%.

EXAMPLE 12

N-([α-phenyl]-n-propyl)-4-pyridinamine 5.4 Grams (0.03 mole) of 4-(benzylidineamino) pyridine in 20 milliliters of dry ether was added to a stirred solution of ethyl lithium (from 3.6 grams ethyl bromide and 0.42 grams of lithium) in 50 milliliters of ether under a nitrogen atmosphere at −10° C. The reaction mixture was allowed to warm to room temperature and after 1 hour decomposed by the addition of water. A solid precipitated and was dissolved by adding toluene. The organic phase was separated and the basic material was extracted with 2 N hydrochloric acid. The acid extracts were basified with 5 N sodium hydroxide solution and extracted into toluene. The toluene extracts were dried ($MgSO_4$) and the solvent was evaporated. The oil which remained was crystallised from a mixture of toluene and light petroleum (boiling point 60°-80° C.) to afford 3.43 grams of white crystals of the title compound, melting point 112° to 114° C.

Analysis: Found: C, 79.2%; H, 7.6%; N, 13.3%. $C_{14}H_{16}N_2$ requires C, 79.21%, H, 7.6%; N, 13.2%.

A solution of the base in hot isopropanol was treated with hydrogen bromide in ether to give 3.33 grams of the title compound as its hydrobromide salt, melting point 190°-192° C.

EXAMPLE 13

N-[(10,11-dihydro-5H-dibenzo[a,d]-cyclohepten-5-yl)methyl]-4-pyridinamine

Diborane was generated by the dropwise addition over 1½ hours at room temperature of a solution of 1.14 grams (30 millimoles) of sodium borohydride in 30 cc. of dry diglyme to a mixture of 6.2 cc. (7.1 grams, 50 millimoles) of redistilled boron trifluoride etherate and 6.2 cc of dry diglyme. The evolved diborane was swept in a slow stream of dry nitrogen into a solution of 3.14 grams (10 millimoles) of N-[(10,11-dihydro-5H-dibenzo[a,d] cyclohepten-5-yl)carbonyl]-4-pyridinamine in 50 cc. of dry tetrahydrofuran, cooled in ice. After complete addition of the borohydride solution, the generator flask was heated to 70°-80° for ½ hour to complete the generation of diborane, which was swept into the reduction mixture as before. The reduction mixture was stirred at 0° for a further hour and was then heated to reflux for 3 hours, maintaining the nitrogen atmosphere. The apparatus was then sealed and allowed to cool overnight. 5 Milliliters of 6 N hydrochloric acid were then added dropwise with care to the reduction mixture, resulting in vigorous hydrogen evolution. The acid solution was then evaporated to dryness to remove tetrahydrofuran and the residue was treated with 25 cc. of water, basified to pH9 with potassium carbonate, filtered, and the filtrate was extracted repeatedly with dichloromethane. The combined organic extracts were dried using $MgSO_4$ and evaporated, leaving 3.02 grams of a yellow oil whose IR spectrum contained no C=O absorption. This oil was taken up in a mixture of propan-2-ol, methanol and dichloromethane, made acid with ethereal hydrogen chloride, filtered and concentrated to 15 cc. On cooling N-](10,11-dihydro-5H-dibenzo[a,d]cyclohepten-5-yl)methyl]-4-pyridinamine, hydrochloride was deposited as colourless crystals (1.58 g, 42%), mp 245°–6° with effervescence.

Analysis Found: C, 75.0%; H, 6.3%; N, 8.1%. $C_{21}H_{20}N_2.HCl$ requires C, 74.9%; H, 6.3%; N, 8.3%.

The N-[(10,11-dihydro-5H-dibenzo[a,d]cyclohepten-5-yl) carbonyl]-4-pyridinamine starting material was prepared as follows:

A solution of 4.7 grams (50 milliliters) of 4-aminopyridine in 50 cc of dry pyridine was treated dropwise at room temperature with a solution of 6.6 grams of 10,11-dihydro-5H-dibenzo[a,d]cyclohepten-5-ylcarbonyl chloride (M. A. Davis, Stanley O. Winthrop, J. Steward, F. A. Sunahara, and F. Herr, J. Medicin. Chem. 1963, 6, 251–5) in 50 cc of toluene. After the exothermic reaction subsided the mixture was stirred at room temperature for 4 hours and was then poured into 30 cc of water. 100 milliliters of toluene were added and the phases were separated. The toluene phase was washed once with 100 cc of water, then the combined aqueous phases were back-extracted with toluene (3×100 cc). The combined toluene solutions were dried($MgSO_4$) and evaporated, leaving an oily residue which was evaporated several times with further toluene and finally once with ethanol to remove residual pyridine, giving 8.45 grams of a yellow solid. This solid was crystallised from toluene (charcoal) giving off-white crystals (4.78 g, 61%), mp 145°–6° ; second crop, off-white crystals (0.96 g, 12%), mp 145°–7.5° .

Both crops were indicated by infrared spectroscopy to control a trace of carboxylic acid (C═O at 1700 cm), so both fractions were combined, dissolved in toluene (150 cc) and washed with 2 N sodium hydroxide solution (3×25 cc) water (3×25 cc) and saturated sodium chloride solution (2×25 cc), and dried (MgSO$_4$). The solution was filtered, concentrated to 50 cc, and allowed to crystallise, giving 4.64 grams (57% yield) of N-[(10,11-dihydro-5H-dibenzo [a,d]cyclohepten-5-yl)carbonyl]-4-pyridinamine as colourless crystals, mp. 148°–9°.

Analysis Found: C, 80.5%; H, 6.0%; N, 9.0%. $C_{21}H_{18}N_2O$ requires C, 80.2%; H, 5.8%; N, 8.9%.

EXAMPLE 14

N-(diphenylmethyl)-N-methyl-4-pyridinamine

A solution of 2.6 grams (0.01 mole) of N-(diphenylmethyl)-4-pyridinamine in 100 milliliters of dry tetrahydrofuran was added at −10° C. to a solution of lithium diisopropylamide (prepared from 1.5 milliliters (0.01 mole) of diisopropylamine and butyl lithium in hexane (7.7 milliliters; 0.01 mole) at −20° C.) in 100 milliliters of tetrahydrofuran, in an atmosphere of nitrogen. The solution was stirred at room temperature for 30 minutes, and then treated with 0.63 milliliters (0.01 mole) of methyl iodide and stirred at room temperature overnight. The solution was decomposed with 5 milliliters of water and evaporated to an oil which was dissolved in propan-2-ol. Acidification with ethereal hydrogen chloride followed by careful addition of ether gave 1.85 grams (56% yield) of N-(diphenylmethyl)-N-methyl-4-pyridinamine hydrochloride monohydrate as white crystals, melting point 215°–220° C.

Analysis: Found C, 69.04%; H, 5.94%; N, 8.86%. $C_{19}H_{18}N_2.HCl.H_2O$ requires C, 69.4%; H, 6.12%; N, 8.52%.

EXAMPLE 15

N-[p-bromo-α-(1-naphthyl)]-4-pyridinamine

The title compound is prepared from 1-naphthyl lithium nd 4-(p-bromobenzylideneamino)pyridine in a manner similar to Examples 5, 6 and 7.

EXAMPLE 16

2-methyl-4-[α-(3,4-methylenedioxyphenol)benzylamino]pyridine

The title compound is prepared from 3,4-methylenedioxyphenyl lithium and 4-(benzylideneamino)-2-methylpyridine in a manner similar to Examples 5,6 and 7.

EXAMPLE 17

N-[(di-m-trifluoromethylphenyl)methyl]-4-pyridinamine

The title compound is prepared from m-trifluoromethylphenyl lithium and 4-(m-trifluoromethylbenzylideneamino)pyridine in a manner similar to Examples 5,6 and 7.

EXAMPLE 18

N-[(α-(2-furyl)-2-thenyl]-4-pyridinamine

The title compound is prepared from 2-furyl lithium (obtained by reacting furan with butyl lithium) and 4-(2-thenylideneamino)pyridine in a manner similar to Examples 5, 6 and 7.

EXAMPLE 19

N-[p-chloro-α(3-furyl)benzyl]-4-pyridinamine

The title compound is prepared in a similar manner to Examples 5,6 and 7 from 3-furyl lithium (obtained by treating 3-iodofuran with butyl lithium) and 4-(p-chlorobenzylideneamino)pyridine.

EXAMPLE 20

N-[m-ethoxy-α-(4-oxazolyl)benzyl]-4-pyridinamine

The title compund is prepared in a similar manner to Examples 5,6 and 7 from 4-oxazolyl lithium (obtained from 4-bromooxazole and butyl lithium) and 4-(m-ethoxybenzylideneamino)pyridine.

EXAMPLE 21

N-[α-(2-oxazolyl)-furfuryl]-4-pyridinamine

The title compound is prepared from 2-oxazolyl lithium (obtained by treating oxazole with butyl lithium) and 4-(furfurylideneamino)pyridine in a similar manner to Examples 5, 6 and 7.

EXAMPLE 22

N-[(5-oxazolyl)(2-pyridyl)methyl]-4-pyridinamine

The title compound is prepared by reacting 4-oxazolyl lithium (obtained from 5-bromooxazole and butyl lithium) with 4-(2-pyridylmethyleneamino)pyridine in a manner similar to Examples 5, 6 and 7.

EXAMPLE 23

N-[3,4-dimethoxy-α-(2-thiazolyl)benzyl]-4-pyridinamine

The title compound is prepared in a similar manner to Examples 5, 6 and 7 by reacting 2-thiazolyl lithium (obtained from 2-bromothiazole and butyl lithium) with 4-(3,4-dimethoxybenzylideneamino)pyridine.

EXAMPLE 24

N-[α-(2-benzthiazolyl)benzyl]-4-pyridinamine

The title compound is prepared in a manner similar to Examples 5, 6 and 7 by reacting 2-benzthiazolyl lithium (formed by treating benzothiazole with butyl lithium) and 4-benzylideneaminopyridine.

EXAMPLE 25

2-Methyl-4-[α-(2-quinolinyl)benzylamine]pyridine

The title compound is prepared in a similar manner to Examples 5, 6 and 7 by reacting 2-quinolyl lithium (formed from 2-chloroquinoline and butyl lithium) with 4-(benzylideneamino)-2-methyl-pyridine.

EXAMPLE 26

N-[α-(5-isothiazolyl)benzyl]-4-pyridinamine

The title compound is prepared in a similar manner to Examples 5, 6 and 7 by reacting 5-isothiazolyl lithium (formed from isothiazole and butyl lithium) with 4-benzylideneaminopyridine.

We claim:

1. A compound selected from those having the formula

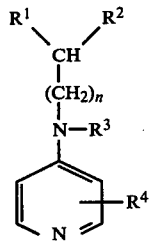

and their pharmaceutically acceptable acid addition salts, wherein one of $R^1$ and $R^2$ is selected from phenyl; naphthyl; phenyl substituted by one or two substituents selected from halogen, lower alkyl, lower alkoxy, lower alkylenedioxy and trifluoromethyl; thienyl; and pyridyl and the other one of $R^1$ and $R^2$ is selected from phenyl; naphthyl; phenyl substituted by one or two substituents selected from halogen, lower alkyl, lower alkoxy, lower alkylenedioxy, trifluoromethyl; thienyl; and pyridyl $R^3$ and $R^4$ are independently selected from hydrogen and lower alkyl and n is selected from 0 and 1.

2. A compound as defined in claim 1, which is selected from N-(diphenylmethyl)-4-pyridinamine and its pharmaceutically acceptable acid addition salts.

3. A compound as defined in claim 1, which is selected from N-[(di-p-fluorophenyl)methyl]-4-pyridinamine and its pharmaceutically acceptable acid addition salts.

4. A compound as defined in claim 1, which is selected from N-[α-(2-methylphenyl)benzyl]-4-pyridinamine and its pharmaceutically acceptable acid addition salts.

5. A compound as defined in claim 1, which is selected from N-[α-(2-thienyl)benzyl]-4-pyridinamine and its pharmaceutically acceptable acid addition salts.

6. A compound as defined in claim 1, which is selected from N-[α-(2-methoxyphenyl)benzyl]-4-pyridinamine and its pharmaceutically acceptable acid addition salts.

7. A compound as defined in claim 1, which is selected from N-[α-(2-pyridyl)benzyl]-4-pyridinamine and its pharmaceutically acceptable acid addition salts.

8. A compound as defined in claim 1, which is selected from N-(2,2-diphenylethyl)-4-pyridinamine and its pharmaceutically acceptable acid addition salts.

9. A compound as defined in claim 1 which is selected from N-(diphenylmethyl)-N-methyl-4-pyridinamine and its pharmaceutically acceptable acid addition salts.

* * * * *